US005911218A

United States Patent [19]
DiMarco

[11] Patent Number: 5,911,218
[45] Date of Patent: Jun. 15, 1999

[54] METHOD AND APPARATUS FOR ELECTRICAL STIMULATION OF THE RESPIRATORY MUSCLES TO ACHIEVE ARTIFICIAL VENTILATION IN A PATIENT

[76] Inventor: Anthony Fortunato DiMarco, 37490 Hunters Ridge, Solon, Ohio 44139

[21] Appl. No.: 08/819,946

[22] Filed: Mar. 18, 1997

Related U.S. Application Data

[63] Continuation of application No. 08/426,301, Apr. 21, 1995, Pat. No. 5,678,535.

[51] Int. Cl.$^6$ ....................................................... A61N 1/36
[52] U.S. Cl. .......................... 128/200.24; 606/32; 607/42
[58] Field of Search ......................... 128/200.24; 606/32, 606/41, 42; 607/2, 3, 42

[56] References Cited

U.S. PATENT DOCUMENTS

| | | |
|---|---|---|
| 2,664,880 | 1/1954 | Wales, Jr. . |
| 2,711,729 | 6/1955 | Hofmann . |
| 3,773,051 | 11/1973 | Holcomb et al. . |
| 3,796,221 | 3/1974 | Hagfors . |
| 3,896,817 | 7/1975 | Hursen et al. . |
| 4,612,934 | 9/1986 | Borkan . |
| 4,827,935 | 5/1989 | Geddes et al. . |
| 4,830,008 | 5/1989 | Meer . |
| 5,056,519 | 10/1991 | Vince . |
| 5,383,913 | 1/1995 | Schiff . |

FOREIGN PATENT DOCUMENTS

| | | |
|---|---|---|
| 2 493 152 | 5/1982 | France . |
| 24 37 346 | 2/1975 | Germany . |
| 86/00234 | 1/1986 | WIPO . |

OTHER PUBLICATIONS

"Exsufflation with Negative Pressure (E.W.N.P.)"; *AMA Archives of Internal Medicine;* H. Bickerman; pp. 698–704.
"Cough Following Transection of Spinal Cord at C–6"; *Archives of Physical Medicine and Rehabilitation;* A. Siebens et al.; pp. 1–8; ©Jan., 1964.
Electrothoracic Artificial Respiration; *Electrothoracic Artificial Respiration;* J. Osterholm et al.; pp. 298–304; ©Oct., 1966.
"Respiratory Complications in Traumatic Quadriplegia"; *J. Neurosurg;* R. Bellamy et al.; vol. 39, pp. 596–600; ©Nov., 1973.
"Cough"; *Arch. Intern. Med.;* R. Irwin et al.; vol. 137, pp. 1186–1191; ©Sep., 1977.
"Pulmonary Dysfunction Following Traumatic Quadriplegia"; *JAMA;* J. McMichan et al.; vol. 243, No. 6, pp. 528–531; ©1980.
"Incidence and Clinical Features of Autonomic Dysreflexia in Patients with Spinal Cord Injury"; *Paraplegia 18;* R. Lindan et al.; pp. 285–292; ©1980.
Detection of Diaphragmatic Fatigue in Man by Phrenic Stimulation; *The American Physiological Society;* M. Aubier et al.; pp. 538–544; ©1981.
"Spinal Cord Electrode for Expiratory Muscle Activation"; Medtronic Neuro; ©Sep., 1982.
"Respiratory Muscle Length Measured by Sonomicrometry"; *The American Physiological Society;* S. Newman et al.; pp. 753–764; ©1984.

(List continued on next page.)

*Primary Examiner*—Mickey Yu
*Assistant Examiner*—Dinh X. Nguyen
*Attorney, Agent, or Firm*—Fay, Sharpe, Beall, Fagan, Minnich & McKee

[57] ABSTRACT

An artificial respirator apparatus periodically activates intercostal muscles in an organism by applying a first stimulation signal while simultaneously activating the diaphragm of the organism by applying a second stimulation signal. The intercostal muscles are stimulated according to a first set of stimulation parameters while the diaphragm is stimulated using a second set of stimulus parameters. The coordinated stimulation of the intercostal muscles and diaphragm effects artificial ventilation in the organism. The stimulation steps are substantially simultaneous and repeated between periods of non-stimulation.

14 Claims, 2 Drawing Sheets

OTHER PUBLICATIONS

"Comparative Effects of Aminophylline on Diaphragm and Cardiac Contractility"; *Am. Ref. Respir. Dis.;* A. F. DiMarco et al.; pp. 800–805; ©Apr., 1985.

"Activation of the Inspiratory Intercostal Muscles by Electrical Stimulation of the Spinal Cord"; A. F. DiMarco et al.; pp. 1385–1390; ©1987.

"Changes in Abdominal Muscle Length During Breathing in Supine Dogs"; *Respiration Physiology;* V. Ninane et al.; vol. 73, pp. 31–40; ©1988.

"Role of Triangularis Sterni During Coughing and Sneezing in Dogs"; *The American Physiological Society;* E. VanLunteren et al.; pp. 2440–2445; ©1988.

"Transverse Abdominis Length Changes During Eupnea, Hypercapnia, and Airway Occlusion"; *The American Physiological Society;* J.S. Arnold et al.; pp. 658–665; ©1988.

"Effect of Hypercapnia and PEEP on Expiratory Muscle EMG and Shortening"; *The American Physiological Society;* A. Oliven et al.; pp. 1408–1413; ©1989.

"Mechanical Response to Hyperinflation of the Two Abdominal Muscle Layers"; *The American Physiological Society;* A.M. Leevers et al.; pp. 2189–2195; ©1989.

"Artificial Ventilation by Means of Electrical Activation of the Intercostal/ Accessory Muscles Alone in Anesthetized Dogs"; *Am. Rev. Respir. Dis.;* A. F. DiMarco et al.; pp. 961–967; ©1989.

Mechanical Action of the Interosseous Intercostal Muscles as a Function of Lung Volume; *Am. Rev. Respir. Dis.;* A. F. DiMarco et al.; pp. 1041–1046; ©1990.

Abdominal Muscle Length During Respiratory Defensive Reflexes; *Respiratory Physiology;* E. VanLunteren et al.; vol. 86; pp. 199–213; ©1991.

"Airway Secretion Clearance by Mechanical Exsufflation for Post–Poliomyelitis Ventilator–Assisted Individuals"; *Arch. Phys. Med. Rehabil.;* J. R. Bach et al.; vol. 75, pp. 170–177; ©Feb., 1993.

"American Review of Respiratory Disease"; 1993 International Conference; vol. 147, No. 4; ©Apr., 1993.

"Evaluation of Intercostal Pacing to Provide Artificial Ventilation in Quadriplegia"; *Am. J. Respir. Crit. Care Med.;* A. F. DiMarco; vol. 150, pp. 934–940; ©1994.

METHOD AND APPARATUS FOR ELECTRICAL STIMULATION OF THE RESPIRATORY MUSCLES TO ACHIEVE ARTIFICIAL VENTILATION IN A PATIENT

This application is a continuation of U.S. application Ser. No. 08/426,301, filed on Apr. 21, 1995, now U.S. Pat. No. 5,678,535.

BACKGROUND OF THE INVENTION

The present invention is directed to a method and apparatus for electrically achieving sustained respiration (ventilation) in a patient. The method is particularly applicable in cases of respiratory paralysis from injury of the spinal cord at the cervical level, but should not be solely limited to such an application. Intermittent electrical stimulation is applied to the phrenic nerves and spinal cord in such a manner as to produce coordinated contraction and relaxation of the diaphragm and the inspiratory intercostal muscles. This results in the restoration of respiration rhythmically through artificial electrical stimulation.

In this regard, normal respiration relates to the act of breathing, i.e., inhaling (inspiration) and exhaling (expiration). It is by the act of breathing that the lungs are supplied with oxygen and carbon dioxide is removed during exhalation.

Specifically, during inspiration, air is inhaled into the lungs and is transferred to the blood by the gaseous exchange that occurs by the capillaries in the walls in the pulmonary alveoli. The oxygen present in the blood is utilized by the tissues resulting in the production of carbon dioxide. The carbon dioxide is in turn removed from the blood by a similar gaseous exchange that occurs at the pulmonary alveoli. During expiration, the carbon dioxide and other related pulmonary gases are removed from the body.

Inspiration or drawing in of air is accomplished by expansion of the thoracic cavity. This is brought about by contraction of the diaphragm and intercostal muscles. The diaphragm is a modified half-dome of numerous musculofibrous tissues separating the thorax and abdomen. The diaphragm is the chief muscle of respiration. The intercostal muscles are the inner and outer layer of muscles between the ribs. These muscles draw adjacent ribs together and act to increase the volume of the thorax during inspiration.

Expiration or the expulsion of air may be active or passive. In ordinary breathing it is passive, through inspiratory muscle relaxation, wherein little muscular effort is needed to bring the chest wall back to normal position. In forced or labored respiration, muscular effort is involved.

If inspiration is accomplished chiefly by contraction of the diaphragm, the abdomen will bulge with each inspiration because the diaphragm, forming at once the floor of the thorax and the roof of the abdominal cavity, is dome-shaped with downwardly directed concavity. In contracting, it pushes the abdominal viscera down. This type of respiration is called diaphragmatic or abdominal. An opposite form of respiration is the thoracic type, in which the ribs and sternum are raised by intercostal muscle contraction.

A respiratory cycle has inspiratory and expiratory phases. At rest the former lasts about one, the latter about three seconds. Increase of thoracic capacity reduces intrapleural pressure and thereby expands the lungs, decreases intrapulmonary pressure and draws air into the respiratory passages. The expiratory phase is largely passive, wherein recoil of the thoracic wall and lungs raises intrathoracic pressure to expel air.

The muscle movements of respiration are generally controlled by the phrenic and intercostal nerves. The ipsilateral phrenic nerve arises in the cervical plexus, enters the thorax and passes to the diaphragm. In essence the phrenic nerve is the motor nerve of the diaphragm.

Previously, in patients suffering from respiratory paralysis from injury of the spinal cord at the cervical level, various attempts have been made to produce artificial respiration. In this regard, electrical stimulation of the phrenic nerves provides a useful tool by which mechanical and contractile performance of the diaphragm can be assessed (Marshall, R. Relationship between stimulus and work of breathing at different lung volumes. *J. Appl. Physiol.* 1962; 17:917–21; Pengelly I. D., Alderson M. A., Milic-Emili J. Mechanics of the diaphragm. *J. Appl. Physiol.* 1971; 30:797–805; Aubier M. Farkas G., DeTroyer A., Mozes R., Roussos C. Detection of diaphragmatic fatigue in man by phrenic stimulation. *J. Appl. Physiol.* 1981; 50:538–44; Danon J., Druz W. S., Goldberg H. B., Sharp J. T. Function of the isolated paced diaphragm and the cervical accessory muscles in C1 quadriplegics. *Am. Rev. Respir. Dis.* 1979; 119:909–18; DeTroyer A., Sampson M., Sigrist S., Macklem P. T. Action of the costal and crural parts of the diaphragm on the rib cage in dogs. *J. Appl. Physiol.* 1982; 53-30-9; DiMarco A. F., Nochomovitz M. L., Altose M. D., Kelsen S. G. Effects of aminophylline on diaphragm and cardiac contractility. *Am. Rev. Respir. Dis.* 1985; 132:800–5).

Further, phrenic nerve stimulation is also a clinically useful method of supporting ventilation in patients with high cervical spinal cord transection (Glenn W. W. 1., Holcomb W. F., Shaw R. K., Hogan J. F., Holschuk K. R. Long term ventilatory support by diaphragm packing in quadriplegia. *Ann. Surg.* 1976; 183:566–77; Glenn W. W. L. The treatment of respiratory paralysis by diaphragm pacing. *Ann. Thorac Surg.* 1980; 30:106–9; Nochomovitz M. I. treated with nocturnal electrophrenic respiration. *Am. Rev. Respir. Dis.* 1978; 117:165–72), and irregular breathing patterns during sleep (Bradley R. D., Day A., Hyland RH, et al. Chronic ventilatory failure caused by abnormal respiratory pattern generation during sleep. *Am. Rev. Respir. Dis.* 1984; 130:678–80).

Unfortunately, activation of the diaphragm alone provides only limited tidal volumes and results in inward displacement of the rib cage (Nochomovitz M. L., DiMarco A. F., Mortimer J. T., Cherniack N. S. Diaphragm activation with intramuscular stimulation in dogs. *Am. Rev. Respir. Dis.* 1983; 127:325–9). The lack of an accurate and reproducible method of eliciting coordinated contraction of the inspiratory intercostal muscles has impeded a comparable evaluation of intercostal muscle mechanics and precluded development of clinical intercostal muscle pacing.

In certain situations phrenic nerve pacing alone has been used to ventilate humans. However, some patients with ventilator dependent quadriplegia do not have sufficient phrenic nerve function to maintain artificial ventilation by conventional phrenic nerve pacing techniques. While intercostal pacing via spinal cord stimulation (SCS) results in substantial inspired volumes (V) as indicated above, this method alone is not always sufficient to maintain artificial ventilation.

SUMMARY OF THE INVENTION

The present invention contemplates a new and improved method and apparatus which overcomes the above-referenced problems and provides for intercostal pacing in combination with diaphragm pacing support. The instant novel pacing technique provides sufficient inspired volume to achieve comfortable full-time support of artificial respiration.

According to the present invention, a method and apparatus for coordinated combined artificial intercostal and diaphragm pacing is provided.

According to a more limited aspect of the invention, the apparatus includes an intercostal muscle stimulator responsive to a first periodic signal for stimulating the intercostal muscles of an organism into motion. A diaphragm stimulator is responsive to a second periodic signal for stimulating the diaphragm of the organism into motion. Lastly, a control unit is connected to the above stimulators for generating the first periodic signal and the second periodic signal in a manner establishing simultaneous motion of the intercostal muscles and the diaphragm muscles of the organism.

According to another aspect of the invention, a method or inducing artificial ventilation in an organism is provided. The method includes stimulating a first group of intercostal muscles in an organism by applying an initial electrical stimulus to the upper thoracic spinal cord of the organism. Substantially simultaneous with the step of stimulating a group of intercostal muscles, at least one hemi-diaphragm of the organism is stimulated by applying a second electrical stimulus to the phrenic nerve of the organism.

According to a still further aspect of the invention, a method of artificial ventilation is provided wherein intercostal muscles of an organism are periodically activated by applying an initial first stimulation signal to the organism. A second stimulation signal is applied to the organism for periodically activating the diaphragm of the organism establishing ventilation.

A primary advantage of the invention resides in the ability to stimulate and sustain artificial ventilation in organisms including humans.

Another advantage of the invention is found in the stimulus parameters which control the intercostal muscles and diaphragm stimulator devices. These parameters are particularly selected to sustain prolonged ventilation in humans while avoiding unnecessary muscle fatigue.

Still other advantages and benefits of the invention will become apparent to those skilled in the art upon a reading and understanding of the following detailed description.

BRIEF DESCRIPTION OF THE DRAWINGS

The invention may take physical form in certain parts and arrangements of parts, preferred embodiments of which will be described in detail in this specification and illustrated in the accompanying drawings which form a part hereof and wherein.

DETAILED DESCRIPTION OF THE PREFERRED EMBODIMENTS

Figure 1:
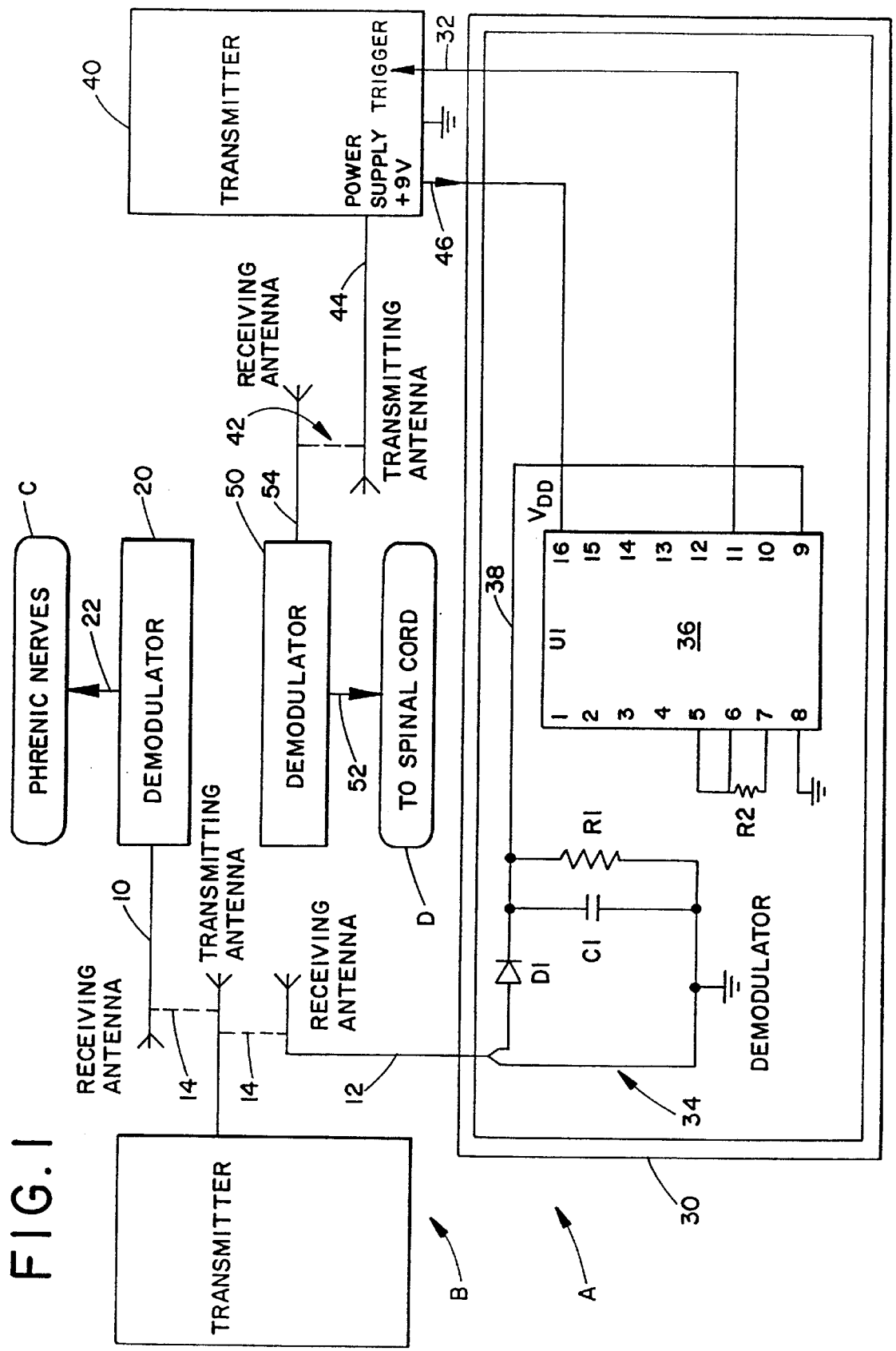
FIG. 1 is a schematic illustration of the subject apparatus for electrically stimulating respiration in a patient.

Referring now to the drawings, wherein showings are for purposes of illustrating the preferred embodiments of the invention only and not for purposes of limiting same, the FIGURES show a pacing apparatus A adapted to receive radio frequency signals from an operatively external radio frequency transmitter B. The pacing apparatus A is connected to a pair of electrodes C and D which are each adapted for placement near the phrenic nerve and on the spinal cord respectively. More particularly with reference to FIG. 1, the pacing apparatus A includes a pair of radio frequency antennas 10 and 12 which are adapted to receive a radio frequency signal 14 from the operatively associated external RF transmitter B. The first RF antenna 10 is connected to a first demodulator circuit 20 which includes the necessary circuitry for demodulating the radio frequency signal from the transmitter B and generating a suitable stimulation pulse on an output signal line 22. The output signal line 22 directs the electrical signal generated in the first demodulator circuit to the phrenic nerve cuff electrode C.

With continued reference to FIG. 1, the pacing apparatus A includes a link-up circuit 30 which is adapted to receive the first radio frequency signal 14 on the antenna 12. The link-up circuit 30 generates a trigger signal on an output signal line 32 when the antenna 12 receives the first RF signal 14 from the transmitter B. The trigger signal on the output signal line 32 is based upon signals generated within the link-up circuit 30 by a tuning circuit 34 and an integrated circuit timer 36. The tuning circuit 34 is of the standard RF tank type including a rectifier D1, a capacitor C1 and a resistor R1. The tuning circuit 34 performs a demodulation function of the first RF signal 14 present on the antenna 12. The tuning circuit 34 generates an output signal on an output line 38 which is in turn interpreted by the intercostal timer circuit 36 to generate the trigger output signal on the output signal line 32.

With further continued reference to FIG. 1, the pacing apparatus A includes a radio frequency transmitter 40 which is adapted to generate a radio frequency signal 42 on an antenna 44 in response to a signal present on the output signal line 32 from the link-up circuit 30. The RF transmitter 40 also includes a built-in power supply for generating and delivering power to the link-up circuit 30 on a power signal line 46.

A second demodulator circuit 50 includes an output signal line 52 for delivering output signals from the demodulator circuit to an electrode D which is adapted for placement on or near a spinal cord of a patient. The second demodulator circuit 50 is adapted to generate stimulation signals in response to receiving the RF signal 42 on an input antenna 54.

The overall operation of the system illustrated in FIG. 1 will now be described. Initially, the radio frequency transmitter B is programmed to periodically generate a first radio frequency signal 14 which was received by the pair of receiving antennas 10 and 12. When that signal is received, the first demodular circuit 20 generates a phrenic nerve stimulation pulse on the output signal line 22 which is connected to a phrenic nerve electrode C.

Simultaneous with the above, the link-up circuit 30 generates an output on the output signal line 32 in response to the first radio frequency signal 14 being received on the radio frequency antenna 12 thereof. The radio frequency transmitter 40 generates a radio frequency signal 42 in response to the signal present on the output signal line 32. Similar to the first demodulator circuit 20, the second demodulator circuit 50 generates an electrical stimulation pulse on an output signal line 52 which is in turn connected to a spinal cord electrode D. Essentially, the stimulation pulses applied to the electrodes C and D are applied substantially simultaneous with each other. However, as would be understood by those skilled in the art, a built in delay may be incorporated into the link-up circuit 30. One example would be to modify the timing functions performed by the intercostal timer 36.

In addition, another modification to the preferred system illustrated in FIG. 1 is to adapt the radio frequency antenna 54 of the second demodulator circuit 50 to respond to the first radio frequency signal 14. In that case, both radio frequency antennas 10 and 54 would simultaneously respond to the single first radio frequency signal 14. Provided that the first radio frequency signal 14 is of sufficient strength, each of the first and second demodulator circuits 20 and 50 could be suitably subcutaneously disposed at their appropriate phrenic nerve and spinal cord locations.

Figures 2, 3:
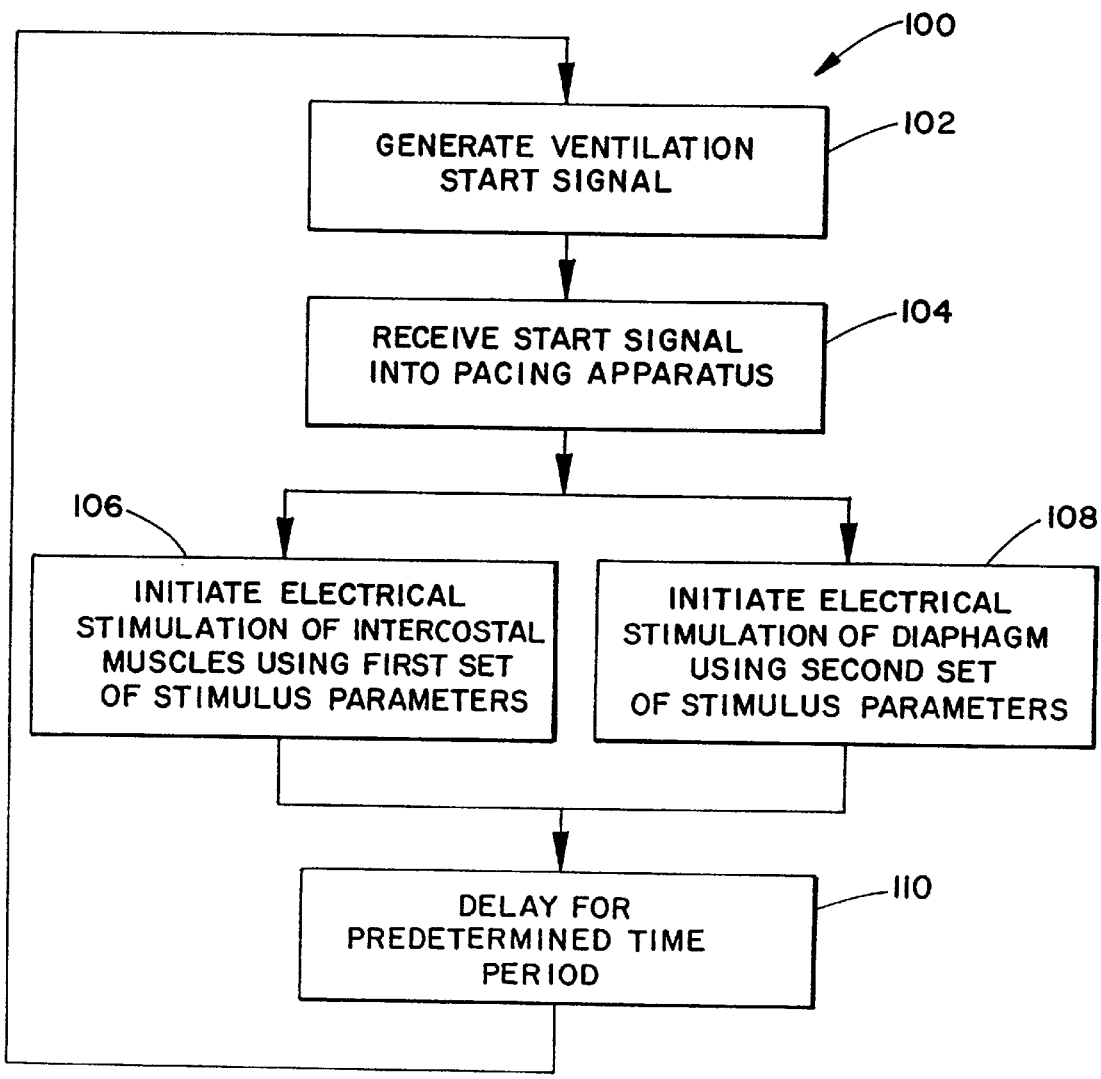
FIG. 2 is a schematic of an electrode used for pacing the intercostal muscle group according to the invention; and, FIG. 3 is a flow chart illustrating the preferred method of stimulating respiration in a patient according to the present invention.

With reference now to FIG. 2, the preferred spinal cord electrode D will be described in detail. In the preferred embodiment of the instant invention any commercially available phrenic nerve cuff electrode may be used and accordingly will not be described in detail in this specification.

With reference then to FIG. 2, the spinal cord electrode D is essentially a modified version of a standard electrode manufacture by Medtronic for use in their spinal cord stimulation (SCS) system. In the preferred electrode illustrated, three electrode plates 62, 64 and 66 are disposed in a silicon rubber insulating body portion 68. Each of the electrode plates 62, 64 and 66 are made from a platinum/iridium or pure platinum composition and are colinearally spaced apart on the body 68 as illustrated. Preferably, the spacing distance is 9 mm between each electrode plate center.

In order to establish an optimal stimulation transfer, each of the electrode plates 62, 64 and 66 are of uniform size and construction. Preferably, the cross-sectional diameters of each of the electrode plates is 4.5 mm. The overall length and width of the insulating silicon rubber body 68 is 35 mm and 7.5 mm respectively.

Each of the electrode plates 62, 64 and 66 are connected to a respective lead wire 72, 74 and 76, respectively. The lead wires exist the body 68 at an exit location 80 which is defined along the length of the body 68. This exit location is preferred over the traditional exit location along the width of the body. One reason for this preferred exit location is that the bundle 82 formed by the lead wires need not be routed around the spinal cord when electrode D is installed but rather need only be routed up to the body 68 away from the spinal cord of the patient.

The electrode D illustrated in FIG. 2 is inserted onto the ventral or dorsal surface of the spinal cord of a patient. The electrode is placed via a laminectomy incision. Connecting wires are attached to the leads forming the bundle 82 forming a percantaneous extension for connection to the second demodulator circuit 50. As described above, the second demodulator circuit includes an antenna 54 and an output signal line 52 for delivering the spinal cord stimulation signals to the electrode D. The anode of the spinal cord electrode is preferably located several centimeters distal to the cathode located on the surface of the spinal cord. In that orientation a broad electric field is generated. The broad electric field induces electrical activity in the spinal cord effecting intercostal muscle stimulation.

The phrenic nerve electrode(s) is (are) positioned on the main trunk of one or both phrenic nerves in either the cervical region via a small neck incision or within the thorax via a thoracotomy incision.

For phrenic nerve packing, commercially available phrenic nerve electrodes, radio frequency receivers and transmitters can be used. Available systems include those manufacture by Avery Laboratories (Glen Cove, N.Y. 11542-1243) Mark IV or S-232G External Transmitter, 902 Antenna, 1-110A Receiver/E-377-05 Electrode (Monopolar) or 1-110 Receiver/E-325 Electrode (Bipolar).

The preferred system is that available diaphragm pacing system manufactured by Atrotech, Inc. (Helsinki, Finland). Phrenic Pacing System (Atrostim Jukka) (Model #RX44-27-2; Controller PX 244).

Although phrenic nerve pacing is an accepted method of providing artificial respiration in patients with chronic respiratory failure secondary to traumatic spinal cord injury (1–3), many ventilator-dependent quadriplegics also have damage to their phrenic motoneuron pools and/or phrenic nerves and consequently cannot be offered artificial ventilation via this technique alone.

It has been demonstrated previously that large inspired volumes can be generated by activation of the intercostal muscles in anesthetized animals (DiMarco A. F., Altose M. D., Cropp A., Durand D. Activation of the inspiratory intercostal muscles by electrical stimulation of the spinal cord. *Am. Rev. Respir. Dis.* 1987; 136:1385–90). This was accomplished by the application of electrical stimuli in the region of the upper thoracic spinal cord via a single electrode. In subsequent studies, it was further demonstrated that the intercostal muscles could be repeatedly activated to provide artificial ventilation for prolonged periods (e.g. >6 hours) while maintaining end-tidal $Pco_2$ in the normal range (DiMarco A. F., Budzinska K., Supinski G. S., Artificial ventilation by means of electrical activation of the intercostal/accessory muscle alone in anesthetized dogs. *Am. Rev. Respir. Dis.* 1989; 139:961–7). With adjustment of stimulus parameters (stimulus amplitude and frequency), these animals could also be hyperventilated for short periods. No evidence of system fatigue was observed in these studies.

The present investigation provides combined intercostal muscle pacing to realize artificial ventilation in ventilator-dependent quadriplegics. The instant invention demonstrates that combined spinal cord stimulation (SCS) and diaphragm pacing results in substantial inspired volume production with few side effects. Inspired volume production by this technique is sufficient to comfortably sustain artificial ventilation for prolonged periods, and is a useful method of enhancing tidal volume in patients with suboptimal volume production via phrenic nerve pacing alone.

Spinal Cord Electrode Placement

A T-4 or T-5 hemilaminectomy procedure is used to position the Medtronic type tripolar spinal cord electrode (7.5 mm ×35 mm) of FIG. 2 on the ventral surface of the upper thoracic spinal cord. The electrode surface comprise these separate leads, each 4 mm in diameter. Because previous animal studies indicated that optimal inspired volume production occurred when stimulation was applied at the T-2 spinal cord level, the center of the electrode is positioned in the midline over this region of the spinal cord. The electrode is positioned in the midline under fluoroscopic guidance to achieve symmetric bilateral contraction of the intercostal muscles.

Radiofrequency Receiver Placement

During a surgical procedure, the two electrode leads 22, 52 from the phrenic nerve electrode and spinal cord electrode are connected to their respective radiofrequency receivers 20, 50. The receivers are then implanted subcutaneously. The first receiver is implanted on the anterior rib cage while the second receiver 50 is also placed over the anterior rib cage to facilitate antenna placement during diaphragm and intercostal muscle stimulation. The anodic portions of the second receiver are connected to indifferent electrodes that were implanted subcutaneously over the back musculature.

A radiofrequency transmitter is then connected to an antenna and positioned over the second receiver for spinal cord stimulation. The external controlling circuitry of this transmitter is adjusted to provide timing parameters suitable for artificial respiration. Cycle on-time and off-time are adjusted to 0.5 to 1.8 seconds and 1 to 5.8 seconds, respectively. Pulse amplitude and stimulus frequency can be varied between 0 and 25 V and 5 and 30 Hz, respectively. Pulse width can be varied between 0.1 and 0.5 ms but should be maintained between 0.05 to 0.3 msec. Pulse train rate (breaths per min) can be varied between 6 and 23. Preferably, the pulse train rate is established at 7–15 breaths/minute.

Muscle Reconditioning

In certain situations, a muscle reconditioning program is necessary. Often, the intercostal muscles are significantly atrophied secondary to disuse and require a period of gradually increasing muscle activation to restore strength and endurance. Consequently, a regimen of intercostal muscle pacing for 5 minutes an hour for 4 to 6 hour a day is necessary. The amount of time per hour and hours per day may be increased over time as tolerated. Stimulus frequency should be maintained at 8–20 Hz because low-frequency stimulation tends to increase the population of fatigue-resistant type 1 fibers (Salmons S., Henriksson J. The adaptive response of skeletal muscle to increased use. *Muscle Nerve* 1981; 4:54–105 and Peckham P. H., Mortimer J. T., Marsolais E. B. Alteration in the force and fatigability of skeletal muscle in quadriplegic humans following exercise induced by chronic electrical stimulation. *Clin. Orthop.* 1976;114:326–34). In patients who cannot tolerate significant time off mechanical ventilatory support and in whom inspired volume production via combined intercostal and diaphragm pacing is insufficient to maintain adequate ventilation, electrical pacing can be performed in conjunction with mechanical ventilation.

Generally, electrical stimuli applied in the region of the upper thoracic spinal cord affect activation of the inspiratory intercostal muscles as well as other muscles of the upper trunk.

Initially, very small changes in airway pressure and inspired volume generation can be expected in response to electrical activation of the spinal cord which is attributable to disuse atrophy of the intercostal muscles. With gradually increasing periods of intercostal muscle stimulation over several weeks, progressive increments in inspiratory pressure generation and inspired volume production result. The pressure-frequency curves, if plotted, shift progressively upward (indicating greater pressure generation for any given stimulus frequency) and to the left (indicating fusion of muscle contraction at lower stimulus frequencies).

Similar Glenn and coworkers (Glenn W. W. L., Hogan J. F., Loke J. S. O., Ciesielski T. E., Phelps M. L., Rowedder R. Ventilatory support by pacing of the conditioned diaphragm in quadriplegia. *N. Engl. J. Med.* 1984;310:1150–5) demonstrated increased diaphragm strength in response to increasing diaphragm pacing in ventilator-dependent quadriplegics during several months of stimulation. With gradually increasing phrenic nerve stimulation, other investigators (Nochomovitz M. L., Hopkins M., Brodkey J., Montenegro H., Mortimer J. T., Cherniack N. S. Conditioning of the diaphragm with phrenic nerve stimulation after prolonged disease. *Am. Reve. Respir. Dis.* 1984; 130:685–8) documented a progressive upward shift of the diaphragm force-frequency relationship over a 4-mo period.

Maximum inspired volume during intercostal pacing alone at 32 Hz and 13 Hz was approximately 730 ml and approximately 500 ml, respectively, in a group of patients who demonstrated substantial improvement following reconditioning. Although difficult to compare with previous studies because of differences in stimulus parameters and patient size, these values are somewhat lower but in the range of that resulting from unilateral diaphragm simulation alone.

According to the present invention, it is possible to maintain full-time ventilatory support in patients with quadriplegia by pacing one hemi-diaphragm separately with low-frequency stimulation (10–15 Hz) at a respiratory rate of 8 to 15 breaths/min while simultaneously pacing the intercostal muscles. In most cases, however, low-stimulus frequencies (10 Hz) and low respiratory rates (9 to 10 breaths/min) are preferred. Although high-frequency stimulation of the intercostal muscles generally result in larger volumes and consequently longer tolerated periods off mechanical support, previous investigators have described myopathic changes in animal diaphragms and reduced diaphragm motion in patients after long-term high-frequency pacing. For these reasons, low-frequency stimulation is preferred. Lower respiratory rates (9 to 10/min) are employed because they are more comfortable and because higher rates interfere significantly with speaking. Glenn and coworkers (Glenn W. W. L., Hogan J. F., Loke J. S. O., Ciesielski T. E., Phelps M. L., Rowedder R. Ventilatory support by pacing of the conditioned diaphragm in quadriplegia. *N. Engl. J. Med.* 1984;310:1150–5) have also recommended diaphragm pacing at low respiratory rates (6 to 9 breaths/min).

It is to be appreciated that the ventilatory requirements for intercostal pacing by spinal cord stimulation (SCS) are sometimes higher than those of diaphragm pacing, because SCS stimulation results in the activation of nonventilatory as well as ventilatory muscles, resulting in greater $CO_2$ production. It is also possible that the intercostal muscles are less efficient than the diaphragm and demand a higher metabolic cost to achieve the same level of ventilation. Intercostal pacing may produce greater paradoxical motion of the noncontracting portion of the chest wall compared with diaphragm pacing. With tetraplegia, rib cage compliance decreases while abdominal compliance increases (10). Consequently, significant abdominal paradox may reduce tidal volume production during intercostal pacing. The reduction in rib cage compliance may minimize the degree of rib cage paradox with diaphragm pacing.

Referring now to FIG. 3, the preferred method for combined intercostal muscle and diaphragm pacing according to the instant invention will be described. Initially, a ventilation start signal is generated 102 by the radio frequency transmitter B. As described above, the start signal 14 is received, at step 104, by the pacing apparatus A on a pair of receiving antennas 10 and 12.

After receiving the ventilation start signal, electrical stimulation of the intercostal muscles are initiated 106 as well as an initiation of the stimulation of the diaphragm 108. As illustrated in the flow chart, the intercostal muscles and diaphragm are substantially simultaneously stimulated. Also, as shown in that FIGURE, and described above, each of the intercostal muscles and diaphragm stimulation functions operate according to a unique set of stimulation parameters.

Once the intercostal muscles and diaphragm are stimulated, a delayed period is entered 110. Basically, the delayed period determines the breathing rate in breaths per minute. After the delay period is exhausted, the control algorithm returns to the ventilation start signal step 102 to realize sustained ventilation of the patient.

Clinical Example of Combined Intercostal and Diaphragm Pacing

A 35 year old male with traumatic quadriplegia ($C_2$–$C_3$) had a right unilateral functioning phrenic nerve pacing system. The left side was non-functional due to phrenic nerve injury. Inspired volumes (V) and negative inspiratory pressure (NIF) during maximum phrenic stimulation were 700 ml and 40 $cmH_2O$, respectively. Inspired volumes during low frequency stimulation (12 Hz) was 360 ml and insufficient to comfortably maintain adequate respiration. An electrode was implanted epidurally on the ventral surface of the upper thoracic spinal cord ($T_2$ level) to activate the intercostal muscles. A link-up circuit detected the phrenic transmitter signal and triggered the intercostal transmitter so that intercostal and diaphragm activation were virtually simultaneous. Following implantation, intercostal stimulation initially resulted in maximum V and NIF of 340 ml and 10 $cmH_2O$, respectively. During a 3–4 month conditioning period of gradual increases in pacing duration, maximum V during intercostal stimulation gradually increased to 700 ml. Intercostal activation was associated with mild contraction of the upper arm muscles and flexion of the hands. Maximum combined intercostal and diaphragm stimulation of either diaphragm or intercostal alone resulted in V of 360 ml and 70 $cmH_2O$. Low frequency stimulation of either diaphragm or intercostal alone resulted in V of 360 ml and, when combined, 720 ml. At a respiratory rate of 9 breaths/min. end-tidal $pCO_2$ was 34 mmHg. Combined diaphragm and intercostal stimulation was capable of sustaining artificial ventilation indefinitely. Our results suggest that in patients with partial phrenic nerve function and inadequate inspired volume, combined intercostal and diaphragm pacing may provide a means of enhancing inspired volume production and providing artificial respiration.

The invention has been described with reference to the preferred embodiments. Modification and alterations will occur to others upon a reading and understanding of this specification. It is my intention to include all such modifications and alterations insofar as they come within the scope of the appended claims or equivalents thereof.

Having thus described the invention, I now claim:

1. An apparatus for electrically stimulating respiration in an organism, said apparatus comprising:

a first radio frequency transmitter for periodically generating a first radio frequency signal;

a first demodulator circuit for receiving and demodulating said first radio frequency signal, said first demodulator circuit including a stimulation pulse output;

a phrenic nerve electrode connected to said stimulation pulse output of said first demodulator circuit;

a link-up circuit for receiving said first radio frequency signal, said link-up circuit including a radio frequency trigger output;

a second radio frequency transmitter connected to said trigger output of said link-up circuit, said second radio frequency transmitter generating a second radio frequency output signal in response to the presence of a trigger input signal;

a second demodulator circuit for receiving and demodulating said second radio frequency signal, said second demodulator circuit having a stimulation pulse output; and, a spinal cord electrode connected to said stimulation pulse output of said second demodulator circuit.

2. An apparatus as set forth in claim 1, wherein said link-up circuit comprises:

an antenna for receiving said first radio frequency signal;

a tuning circuit connected to said antenna for demodulating said first radio frequency signal; and, an intercoastal timing circuit having an input connected to an output of said tuning circuit, said intercoastal timing circuit generating said radio frequency trigger output.

3. An apparatus as set forth in claim 2, wherein said tuning circuit is a radio frequency tank circuit comprising a rectifier, a capacitor, and a resistor.

4. An apparatus as set forth in claim 1, wherein said second radio frequency transmitter includes a power supply for generating and delivering electrical power to said link-up circuit.

5. An apparatus as set forth in claim 1, wherein said spinal cord electrode comprises:

an insulating body; and, a plurality of like electrodes evenly spaced relative to each other in said insulating body.

6. An apparatus as set forth in claim 5, wherein said plurality of like electrodes comprise platinum and are colinearly positioned relative to each other in said insulating body.

7. A method of inducing artificial ventilation in a human comprising:

periodically generating and transmitting a first radio frequency signal;

receiving and demodulating said first radio frequency signal at a first demodulation circuit;

generating a first electrical output stimulation pulse and transmitting said first electrical output stimulation pulse to a phrenic nerve of a human;

receiving and demodulating said first radio frequency signal at a second demodulation circuit;

generating a second electrical output stimulation pulse and transmitting said second electrical output stimulation pulse to a spinal cord of said human.

8. The method as set forth in claim 7, wherein generating said second electrical output stimulation pulse and transmitting said second electrical output stimulation pulse to said spinal cord of said human includes:

generating a trigger output signal from a timing circuit in response to said received first radio frequency signal;

transmitting said trigger output signal from said timing circuit to a second radio frequency transmitter;

generating a second radio frequency signal at said second radio frequency transmitter in response to said trigger output signal;

transmitting said second radio frequency signal to a second radio frequency signal demodulator;

demodulating said second radio frequency signal and generating said second electrical output stimulation pulse in response to said second radio frequency signal.

9. The method as set forth in claim 7, wherein said first and second electrical output stimulation pulses are transmitted substantially simultaneously.

10. The method as set forth in claim 7, wherein said second electrical stimulation pulse is transmitted to said spinal cord a predetermined duration after said first electrical output stimulation pulse in transmitted to said phrenic nerve.

11. The method as set forth in claim 7, wherein said first electrical output stimulation pulse is applied to said phrenic nerve for a first predetermined duration; and, said second electrical output stimulation pulse is applied to an upper thoracic region of said spinal cord for a second predetermined duration.

12. The method as set forth in claim 11, wherein second predetermined duration is approximately 0.5 seconds to approximately 1.8 seconds.

13. The method as set forth in claim 12, wherein said second electrical output stimulation pulse applied to said upper thoracic region is approximately 8 volts to approximately 25 volts.

14. The method as set forth in claim 13, wherein said second electrical output stimulation pulse applied to said upper thoracic region of said spinal cord is approximately 8 milliamperes to approximately 25 milliamperes.

* * * * *